(12) United States Patent
Davis et al.

(10) Patent No.: US 9,629,618 B2
(45) Date of Patent: *Apr. 25, 2017

(54) SPECIMEN RETRIEVAL DEVICE

(71) Applicant: Covidien LP, Mansfield, MA (US)

(72) Inventors: Emily Davis, Cheshire, CT (US);
Thomas Wingardner, III, North Haven, CT (US); Russell Pribanic, Roxbury, CT (US)

(73) Assignee: Covidien LP, Mansfield, MA (US)

( * ) Notice: Subject to any disclaimer, the term of this patent is extended or adjusted under 35 U.S.C. 154(b) by 285 days.

This patent is subject to a terminal disclaimer.

(21) Appl. No.: 14/311,383

(22) Filed: Jun. 23, 2014

(65) Prior Publication Data

US 2014/0303640 A1    Oct. 9, 2014

Related U.S. Application Data

(63) Continuation of application No. 13/438,283, filed on Apr. 3, 2012, now Pat. No. 8,795,291.

(Continued)

(51) Int. Cl.
*A61B 17/00* (2006.01)

(52) U.S. Cl.
CPC ............... *A61B 17/00234* (2013.01); *A61B 2017/00287* (2013.01)

(58) Field of Classification Search
CPC ............ A61B 17/221; A61B 17/00234; A61B 2017/00287; A61B 2017/2215;

(Continued)

(56) References Cited

U.S. PATENT DOCUMENTS 30,471 A    10/1860 Dudley
35,164 A    5/1862 Logan et al.
(Continued)

FOREIGN PATENT DOCUMENTS

CN    1695562 A    11/2005
CN    201005724 Y    1/2008
(Continued)

OTHER PUBLICATIONS

Chinese First Office Action (with English translation), dated Mar. 4, 2015, corresponding to Chinese Application No. 201210134944.9; 11 total pages.

(Continued)

*Primary Examiner* — David C Eastwood

(57) ABSTRACT

A specimen retrieval pouch (pouch) is provided. The pouch including a closed bottom portion, an open upper portion and an elongated tube operably coupled to an interior wall of the pouch. The elongated tube has a plurality of openings positioned along a length thereof. A suture accessible at a proximal end of the pouch is positioned within the elongated tube and extends past a distal end thereof. The suture is movable within the elongated tube and relative to the pouch. The suture has either a needle or a loop at a distal end thereof for attaching to tissue and subsequently drawing the tissue into the pouch when the suture is pulled. One or more reinforced tabs are operably disposed on the pouch. The reinforced tab(s) is/are configured to be grasped by a user to provide a counter pull force as the suture is being pulled through the elongated tube.

16 Claims, 4 Drawing Sheets

Related U.S. Application Data

(60) Provisional application No. 61/480,516, filed on Apr. 29, 2011.

(58) Field of Classification Search
CPC ....... A61B 2017/320024; A61B 2017/320064; A61B 2017/320076; A61J 1/10; A61J 1/12; B01L 3/505
USPC ............ 600/562, 564, 580; 604/163, 164.08, 604/164.12, 271, 327–328, 347, 349, 317, 604/540; 606/110, 114, 127–128, 139, 606/144, 159, 167–180
See application file for complete search history.

(56) References Cited

U.S. PATENT DOCUMENTS

| | | |
|---|---|---|
| 156,477 A | 11/1874 | Bradford |
| 1,609,014 A | 11/1926 | Dowd |
| 3,800,781 A | 4/1974 | Zalucki |
| 4,557,255 A | 12/1985 | Goodman |
| 4,611,594 A | 9/1986 | Grayhack et al. |
| 4,744,363 A | 5/1988 | Hasson |
| 4,790,812 A | 12/1988 | Hawkins, Jr. et al. |
| 4,852,586 A | 8/1989 | Haines |
| 4,927,427 A | 5/1990 | Kriauciunas et al. |
| 4,977,903 A | 12/1990 | Haines |
| 4,991,593 A | 2/1991 | LeVahn |
| 4,997,435 A | 3/1991 | Demeter |
| 5,037,379 A | 8/1991 | Clayman et al. |
| 5,074,867 A | 12/1991 | Wilk |
| 5,084,054 A | 1/1992 | Bencini et al. |
| 5,143,082 A | 9/1992 | Kindberg et al. |
| 5,147,371 A | 9/1992 | Washington et al. |
| 5,176,687 A | 1/1993 | Hasson et al. |
| 5,190,542 A | 3/1993 | Nakao et al. |
| 5,190,555 A | 3/1993 | Wetter et al. |
| 5,190,561 A | 3/1993 | Graber |
| 5,192,284 A | 3/1993 | Pleatman |
| 5,192,286 A | 3/1993 | Phan et al. |
| 5,201,740 A | 4/1993 | Nakao et al. |
| 5,215,521 A | 6/1993 | Cochran et al. |
| 5,224,930 A | 7/1993 | Spaeth et al. |
| 5,234,439 A | 8/1993 | Wilk et al. |
| 5,279,539 A | 1/1994 | Bohan et al. |
| 5,312,416 A | 5/1994 | Spaeth et al. |
| 5,330,483 A | 7/1994 | Heaven et al. |
| 5,336,227 A | 8/1994 | Nakao et al. |
| 5,337,754 A | 8/1994 | Heaven et al. |
| 5,341,815 A | 8/1994 | Cofone et al. |
| 5,352,184 A | 10/1994 | Goldberg et al. |
| 5,354,303 A | 10/1994 | Spaeth et al. |
| 5,368,545 A | 11/1994 | Schaller et al. |
| 5,368,597 A | 11/1994 | Pagedas |
| 5,370,647 A | 12/1994 | Graber et al. |
| 5,383,888 A | 1/1995 | Zvenyatsky et al. |
| 5,443,472 A | 8/1995 | Li |
| 5,465,731 A | 11/1995 | Bell et al. |
| 5,480,404 A | 1/1996 | Kammerer et al. |
| 5,486,182 A | 1/1996 | Nakao et al. |
| 5,486,183 A | 1/1996 | Middleman et al. |
| 5,499,988 A | 3/1996 | Espiner et al. |
| 5,524,633 A | 6/1996 | Heaven et al. |
| 5,535,759 A | 7/1996 | Wilk |
| 5,578,048 A | 11/1996 | Pasqualucci et al. |
| 5,611,803 A | 3/1997 | Heaven et al. |
| 5,618,294 A | 4/1997 | Aust et al. |
| 5,618,296 A | 4/1997 | Sorensen et al. |
| 5,630,822 A | 5/1997 | Hermann et al. |
| 5,642,282 A | 6/1997 | Sonehara |
| 5,643,282 A | 7/1997 | Kieturakis |
| 5,643,283 A | 7/1997 | Younker |
| 5,645,083 A | 7/1997 | Essig et al. |
| 5,647,372 A | 7/1997 | Tovey et al. |
| 5,649,902 A | 7/1997 | Yoon |
| 5,658,296 A | 8/1997 | Bates et al. |
| 5,679,423 A | 10/1997 | Shah |
| 5,735,289 A | 4/1998 | Pfeffer et al. |
| 5,755,724 A | 5/1998 | Yoon |
| 5,759,187 A | 6/1998 | Nakao et al. |
| 5,769,794 A | 6/1998 | Conlan et al. |
| 5,785,677 A | 7/1998 | Auweiler |
| 5,788,709 A | 8/1998 | Riek et al. |
| 5,792,145 A | 8/1998 | Bates et al. |
| 5,814,044 A | 9/1998 | Hooven |
| 5,829,440 A | 11/1998 | Broad, Jr. |
| 5,836,953 A | 11/1998 | Yoon |
| 5,853,374 A | 12/1998 | Hart et al. |
| 5,895,392 A | 4/1999 | Riek et al. |
| 5,906,621 A | 5/1999 | Secrest et al. |
| 5,908,429 A | 6/1999 | Yoon |
| 5,944,727 A | 8/1999 | Ahari et al. |
| 5,957,884 A | 9/1999 | Hooven |
| 5,971,995 A | 10/1999 | Rousseau |
| 5,980,544 A | 11/1999 | Vaitekunas |
| 5,997,547 A | 12/1999 | Nakao et al. |
| 6,004,330 A | 12/1999 | Middleman et al. |
| 6,007,512 A | 12/1999 | Hooven |
| 6,007,546 A | 12/1999 | Snow et al. |
| 6,019,770 A | 2/2000 | Christoudias |
| 6,036,681 A | 3/2000 | Hooven |
| 6,059,793 A | 5/2000 | Pagedas |
| 6,123,701 A | 9/2000 | Nezhat |
| 6,152,932 A | 11/2000 | Ternstrom |
| 6,162,235 A | 12/2000 | Vaitekunas |
| 6,165,121 A | 12/2000 | Alferness |
| 6,168,603 B1 | 1/2001 | Leslie et al. |
| 6,228,095 B1 | 5/2001 | Dennis |
| 6,270,505 B1 | 8/2001 | Yoshida et al. |
| 6,277,083 B1 | 8/2001 | Eggers et al. |
| 6,280,450 B1 | 8/2001 | McGuckin, Jr. |
| 6,344,026 B1 | 2/2002 | Burbank et al. |
| 6,348,056 B1 | 2/2002 | Bates et al. |
| 6,350,266 B1 | 2/2002 | White et al. |
| 6,350,267 B1 | 2/2002 | Stefanchik |
| 6,383,195 B1 | 5/2002 | Richard |
| 6,383,196 B1 | 5/2002 | Leslie et al. |
| 6,383,197 B1 | 5/2002 | Conlon et al. |
| 6,406,440 B1 | 6/2002 | Stefanchik |
| 6,409,733 B1 | 6/2002 | Conlon et al. |
| 6,419,639 B2 | 7/2002 | Walther et al. |
| 6,447,523 B1 | 9/2002 | Middleman et al. |
| 6,471,659 B2 | 10/2002 | Eggers et al. |
| 6,506,166 B1 | 1/2003 | Hendler et al. |
| 6,508,773 B2 | 1/2003 | Burbank et al. |
| 6,537,273 B1 | 3/2003 | Sosiak et al. |
| 6,589,252 B2 | 7/2003 | McGuckin, Jr. |
| 6,752,811 B2 | 6/2004 | Chu et al. |
| 6,755,779 B2 | 6/2004 | Vanden Hoek et al. |
| 6,780,193 B2 | 8/2004 | Leslie et al. |
| 6,805,699 B2 | 10/2004 | Shimm |
| 6,840,948 B2 | 1/2005 | Albrecht et al. |
| 6,872,211 B2 | 3/2005 | White et al. |
| 6,887,255 B2 | 5/2005 | Shimm |
| 6,994,696 B2 | 2/2006 | Suga |
| 7,052,454 B2 | 5/2006 | Taylor |
| 7,052,501 B2 | 5/2006 | McGuckin, Jr. |
| 7,090,637 B2 | 8/2006 | Danitz et al. |
| 7,115,125 B2 | 10/2006 | Nakao et al. |
| 7,270,663 B2 | 9/2007 | Nakao |
| 7,273,488 B2 | 9/2007 | Nakamura et al. |
| 7,325,546 B2 | 2/2008 | Burbank et al. |
| 7,410,491 B2 | 8/2008 | Hopkins et al. |
| 7,547,310 B2 | 6/2009 | Whitfield |
| 7,670,346 B2 | 3/2010 | Whitfield |
| 7,762,959 B2 | 7/2010 | Bilsbury |
| 7,819,121 B2 | 10/2010 | Amer |
| 7,837,612 B2 | 11/2010 | Gill et al. |
| 8,579,914 B2 | 11/2013 | Menn et al. |
| 8,795,291 B2 | 8/2014 | Davis et al. |
| 2003/0100909 A1 | 5/2003 | Suzuki |
| 2004/0097960 A1 | 5/2004 | Terachi et al. |
| 2004/0138587 A1* | 7/2004 | Lyons, IV ........ A61B 17/00234 600/562 |
| 2005/0165411 A1 | 7/2005 | Orban |

(56) References Cited

U.S. PATENT DOCUMENTS

| | | |
|---|---|---|
| 2005/0267492 A1 | 12/2005 | Poncet et al. |
| 2006/0030750 A1 | 2/2006 | Amer |
| 2006/0052799 A1 | 3/2006 | Middleman et al. |
| 2006/0058776 A1 | 3/2006 | Bilsbury |
| 2006/0169287 A1 | 8/2006 | Harrison et al. |
| 2006/0199999 A1 | 9/2006 | Ikeda et al. |
| 2006/0200169 A1 | 9/2006 | Sniffin |
| 2006/0200170 A1 | 9/2006 | Aranyi |
| 2006/0229639 A1 | 10/2006 | Whitfield |
| 2006/0229640 A1 | 10/2006 | Whitfield |
| 2007/0016224 A1 | 1/2007 | Nakao |
| 2007/0016225 A1 | 1/2007 | Nakao |
| 2007/0073251 A1 | 3/2007 | Zhou et al. |
| 2007/0088370 A1 | 4/2007 | Kahle et al. |
| 2007/0135780 A1 | 6/2007 | Pagedas |
| 2007/0135781 A1 | 6/2007 | Hart |
| 2007/0186935 A1 | 8/2007 | Wang et al. |
| 2008/0177214 A1 | 7/2008 | Robertsson et al. |
| 2008/0188766 A1 | 8/2008 | Gertner |
| 2008/0221588 A1 | 9/2008 | Hollis et al. |
| 2008/0234696 A1 | 9/2008 | Taylor et al. |
| 2008/0300613 A1 | 12/2008 | Shelton, IV et al. |
| 2008/0300621 A1 | 12/2008 | Hopkins et al. |
| 2008/0312496 A1 | 12/2008 | Zwolinski |
| 2009/0082779 A1 | 3/2009 | Nakao |
| 2009/0182292 A1 | 7/2009 | Egle et al. |
| 2009/0192510 A1 | 7/2009 | Bahney |
| 2009/0192518 A1 | 7/2009 | Golden et al. |
| 2009/0240238 A1 | 9/2009 | Grodrian et al. |
| 2010/0000471 A1 | 1/2010 | Hibbard |
| 2011/0184434 A1 | 7/2011 | Parihar et al. |
| 2011/0184436 A1 | 7/2011 | Shelton, IV et al. |
| 2011/0190781 A1 | 8/2011 | Collier et al. |
| 2011/0190782 A1* | 8/2011 | Fleming ............ A61B 17/00234 606/114 |
| 2011/0299799 A1 | 12/2011 | Towe |
| 2012/0046667 A1 | 2/2012 | Cherry et al. |
| 2012/0083795 A1 | 4/2012 | Fleming et al. |
| 2013/0023895 A1 | 1/2013 | Saleh |

FOREIGN PATENT DOCUMENTS

| | | |
|---|---|---|
| DE | 3542667 A1 | 6/1986 |
| DE | 8435489 U1 | 8/1986 |
| DE | 4204210 A1 | 8/1992 |
| DE | 19624826 A1 | 1/1998 |
| EP | 0947166 A2 | 10/1999 |
| EP | 1685802 A1 | 8/2006 |
| EP | 1707126 A1 | 10/2006 |
| EP | 2005900 A2 | 12/2008 |
| EP | 2184014 A2 | 5/2010 |
| EP | 2353510 A2 | 8/2011 |
| FR | 1272412 A | 9/1961 |
| GB | 2460099 A | 11/2009 |
| WO | 9315675 A1 | 8/1993 |
| WO | 9509666 A1 | 4/1995 |
| WO | 01/35831 A1 | 5/2001 |
| WO | 2004002334 A1 | 1/2004 |
| WO | 2004/112571 A2 | 12/2004 |
| WO | 2005112783 A1 | 12/2005 |
| WO | 2006/110733 | 10/2006 |
| WO | 2007/048078 A1 | 4/2007 |
| WO | 2007/048085 A2 | 4/2007 |
| WO | 2008/114234 A2 | 9/2008 |
| WO | 2009055791 A2 | 4/2009 |
| WO | 2009/149146 A1 | 12/2009 |
| WO | 2011/090862 A2 | 7/2011 |

OTHER PUBLICATIONS

European Search Report for EP 12165852.0-1269 date of completion is Jun. 13, 2012 (6 pages).
Partial International Search Report corresponding to EP 12191639.9, mailed Feb. 20, 2013; 6 pp.
Extended European Search Report corresponding to EP No. 11 25 0837.9, completed Sep. 3, 2013 and mailed Sep. 10, 2013: (7 pp).
Extended European Search Report corresponding to EP No. 11 25 0838.7, completed Sep. 3, 2013 and mailed Sep. 10, 2013; (5 pp).
Extended European Search Report corresponding to EP No. 13 17 0118.7. completed Nov. 25, 2013 and mailed Dec. 5, 2013; (10 pp).
http://www.biomaterials.org/week/bio17.cfm, definition and examples of hydrogels, retrieved Jan. 31, 2014.
European Search Report EP 12150271 dated Jan. 14, 2013.
European Search Report EP 12193450 dated Feb. 27, 2013.
European Search Report EP 12189517.1 dated Mar. 6, 2013.
European Search Report EP 12158873 dated Jul. 19, 2012.
European Search Report EP 11250836 dated Sep. 12, 2013.
European Search Report EP 11250114.3 dated Feb. 10, 2014.
European Search Report EP 12165852 dated Jun. 20, 2012.

* cited by examiner

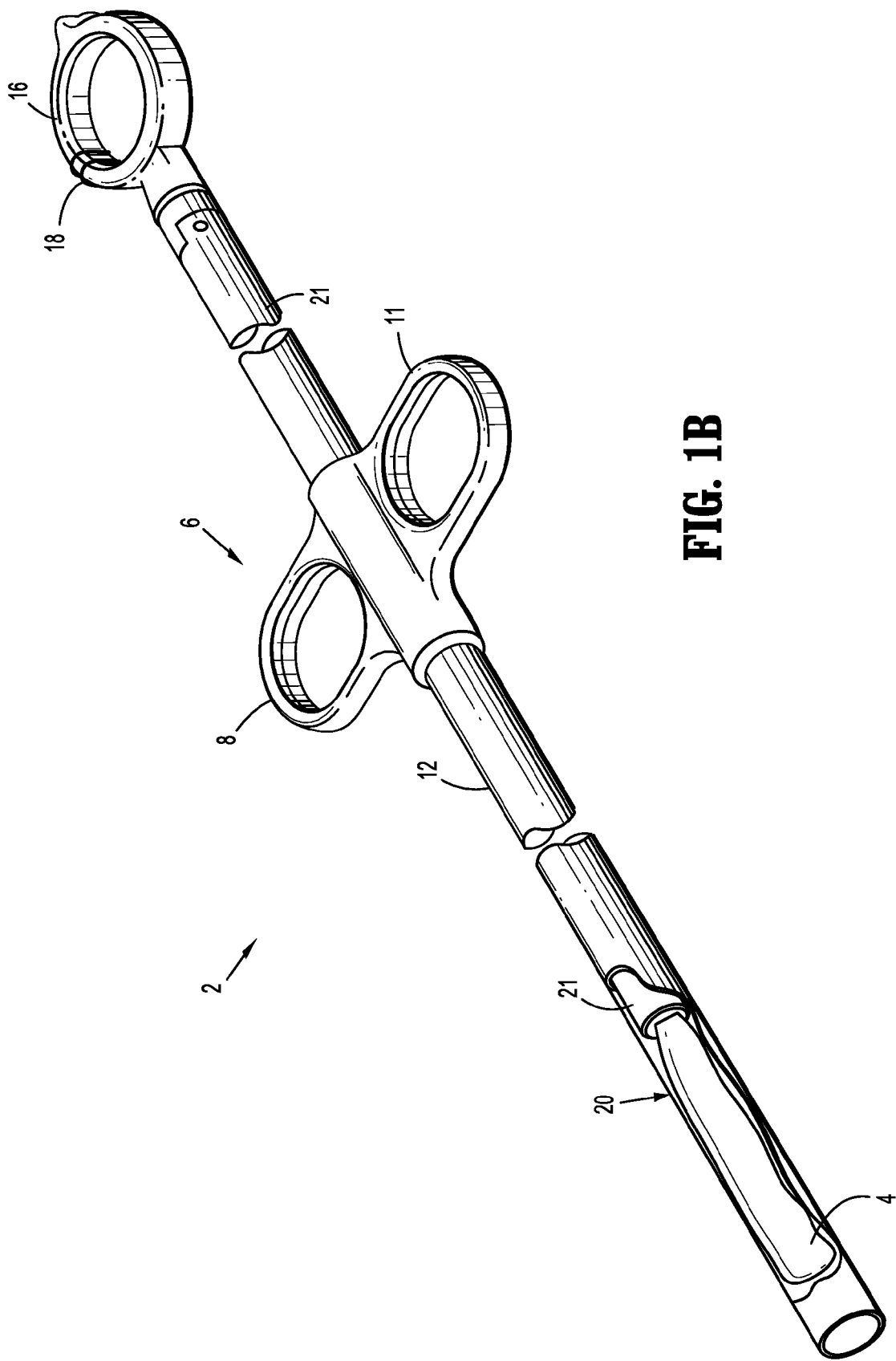

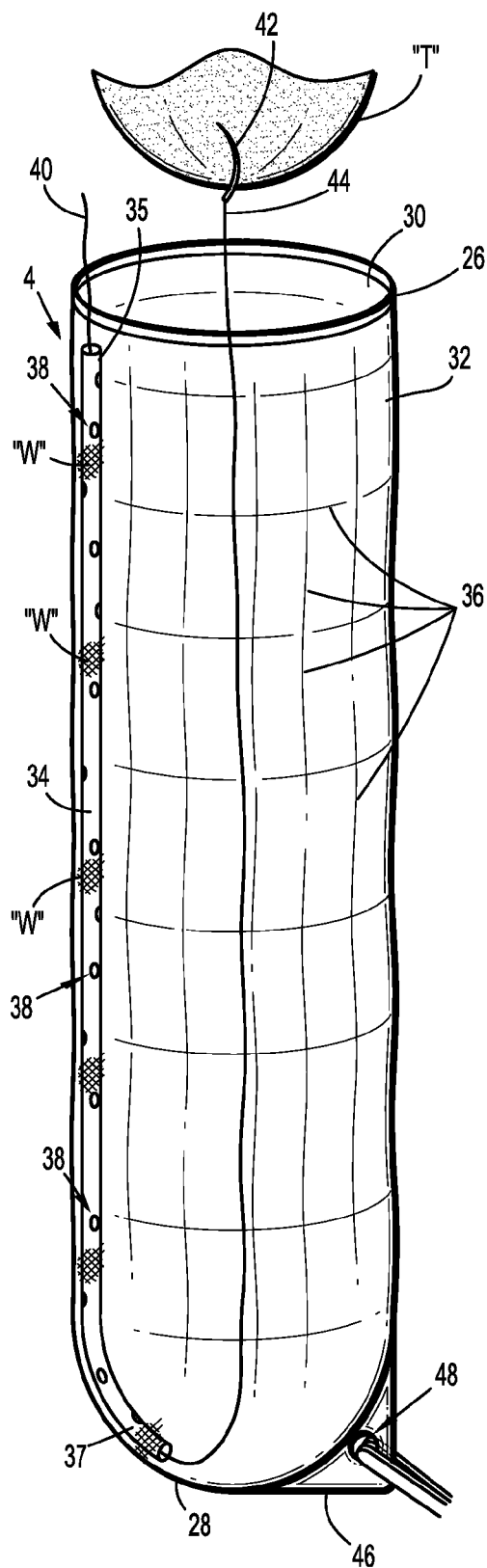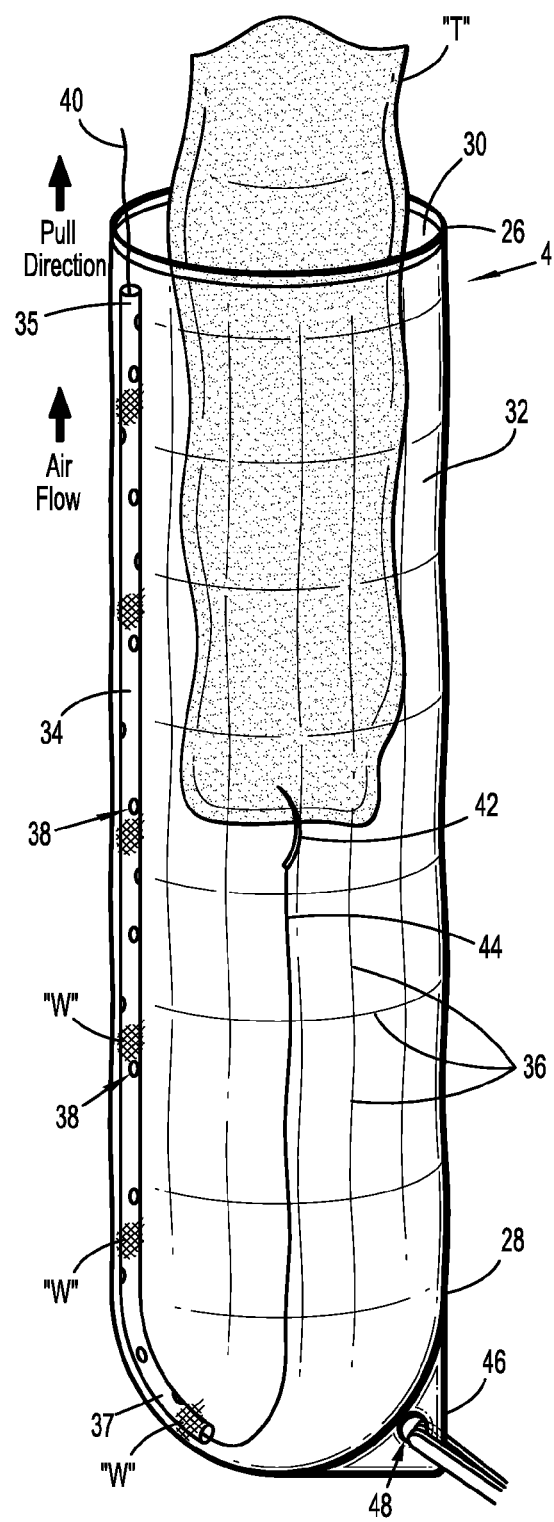
FIG. 2  FIG. 3

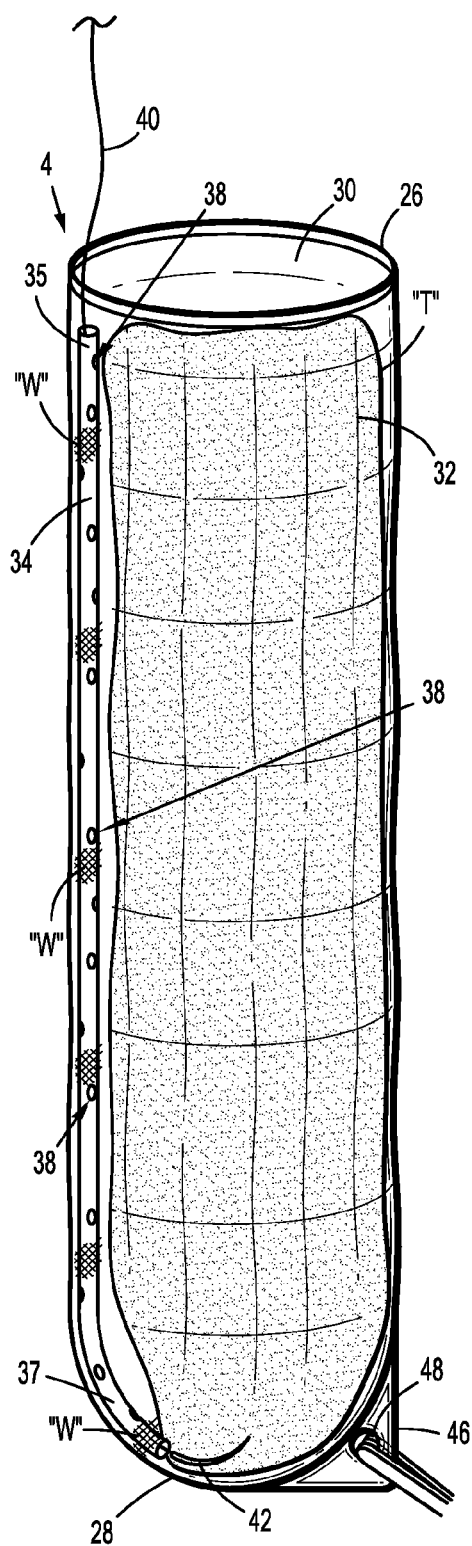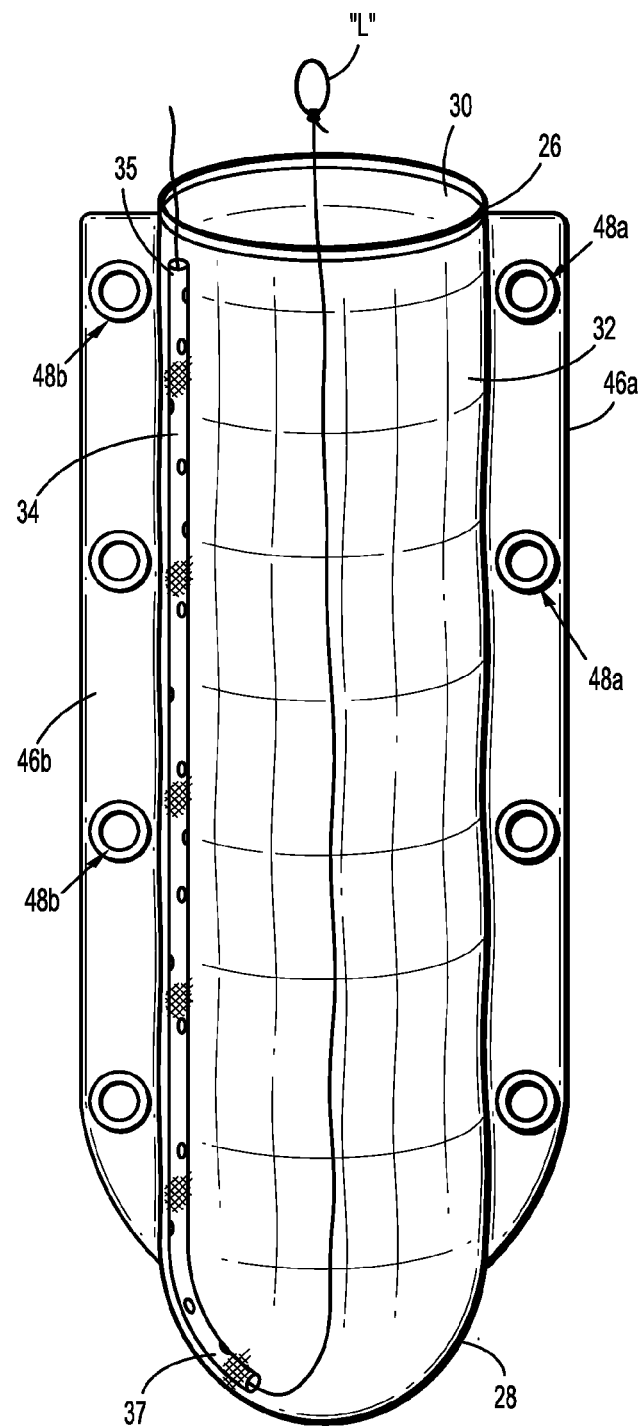
FIG. 4　　　FIG. 5

SPECIMEN RETRIEVAL DEVICE

CROSS REFERENCE TO RELATED APPLICATIONS

The present application is a continuation application of U.S. patent application Ser. No. 13/438,283 filed on Apr. 3, 2012, which claims the benefit of and priority to U.S. Provisional Application Ser. No. 61/480,516 filed by Davis et al. on Apr. 29, 2011, the entire contents of which is hereby incorporated by reference.

BACKGROUND

Technical Field

The present disclosure relates to a specimen retrieval device. More particularly, the present disclosure relates to a specimen retrieval device configured for use in minimally invasive surgical procedures.

Background of Related Art

Laparoscopic and endoscopic surgical procedures are minimally invasive procedures in which operations are carried out within the body by means of elongated instruments inserted through a relatively small entrance or access openings in the body, e.g., an opening defined by a natural passageway of the body, an opening created by a tissue piercing instrument (e.g., a trocar), etc.

Minimally invasive procedures are often used to partially or totally remove body tissue or organs from the interior of the body, e.g. nephrectomy, cholecystectomy, duodenectomy, ileectomy, jejunectomy and other such procedures. During such procedures, it is common that affected tissue or organ must be removed via the access opening in the skin, or through a cannula. Various types of entrapment devices are known in the art to facilitate this procedure, such as, for example, specimen retrieval bags or pouches.

Specimen retrieval bags typically include a layer of puncture-resistant material, a layer of moisture-resistant material and a drawstring. In certain instances, the specimen retrieval bag may be equipped with a morcellator that is utilized to chop or otherwise treat tissue placed in the specimen retrieval bag. In use, the specimen retrieval bag is placed within a body cavity. The body tissue or organ is placed within the specimen retrieval bag. Thereafter, the specimen retrieval bag may be pulled out of the body cavity through the incision in the skin.

In certain instances, however, the body tissue or organ placed in conventional specimen retrieval bags may gather and bulge (such as, for example, in this instance where longer length tissue is placed in the retrieval bag) at the bottom of the specimen retrieval bag making it sometimes difficult to remove the specimen retrieval bag from the relatively small access opening. In addition, air may get trapped in the specimen retrieval bag and, thus, may add to the overall volume of the specimen retrieval bag; as can be appreciated this may also make it difficult to remove the specimen retrieval bag from the relatively small access opening. Moreover, to remove conventional specimen retrieval bags through the access opening, a user, typically, applies a pull force at a single point (i.e., point where drawstring attaches to the specimen retrieval pouch), thus, there exists the likelihood of the specimen retrieval bag tearing at this point.

In view of the foregoing, there remains a need for an improved specimen retrieval device that is configured to facilitate tissue removal in minimally invasive surgical procedures.

SUMMARY

The present disclosure provides a specimen retrieval pouch configured for use with one or more surgical instruments for positioning tissue within the specimen retrieval pouch. The specimen retrieval pouch including a closed bottom portion and an open upper portion. The specimen retrieval pouch includes an elongated tube operably coupled to an interior wall and extends along a length thereof. The elongated tube has a plurality of openings positioned along a length thereof. A suture is accessible at a proximal end of the specimen retrieval pouch positioned within the elongated tube extends past a distal end thereof. The suture is movable within the elongated tube and relative to the specimen retrieval pouch. The suture has either a needle or a knot at a distal end thereof for attaching to tissue and subsequently drawing the tissue into the specimen retrieval pouch when the suture is pulled though the elongated tube. One or more reinforced tabs are operably disposed on the specimen retrieval pouch. The reinforced tab(s) is/are configured to be grasped by a user to provide a counter pull force as the suture is being pulled through the elongated tube.

The present disclosure provides a specimen retrieval device. The specimen retrieval device includes an applicator. A specimen retrieval pouch is operably disposed within the applicator and deployable therefrom. The specimen retrieval pouch defines a longitudinal axis therethrough and includes a closed bottom portion and an open upper portion. The specimen retrieval pouch includes an elongated tube extending along a length thereof. The elongated tube has a plurality of openings positioned along a length thereof. A suture is positioned within the specimen retrieval pouch and is accessible at a proximal end thereof. The suture configured to attach to tissue for drawing the tissue into the specimen retrieval pouch when the suture is pulled though the elongated tube.

The present disclosure provides a specimen retrieval device. The specimen retrieval device includes an applicator. A specimen retrieval pouch is operably disposed within the applicator and deployable therefrom. The specimen retrieval pouch defines a longitudinal axis therethrough and includes a closed bottom portion and an open upper portion. The specimen retrieval pouch includes an elongated tube operably coupled to an interior wall and extends along a length thereof. The elongated tube has a plurality of openings positioned along a length thereof. A suture is accessible at a proximal end of the specimen retrieval pouch and positioned within the elongated tube extends past a distal end thereof. The suture is movable within the elongated tube and relative to the specimen retrieval pouch for attaching to tissue and subsequently drawing the tissue into the specimen retrieval pouch when the suture is pulled.

BRIEF DESCRIPTION OF THE DRAWINGS

Embodiments of the presently disclosed specimen retrieval apparatus are described hereinbelow with reference to the drawings wherein:

FIG. 1B is a partial, perspective view of the specimen retrieval device depicted in FIG. 1A with the specimen retrieval pouch positioned therein;

FIG. 2 is a perspective view of the specimen retrieval pouch depicted in FIG. 1A;

FIG. 3 is a perspective view of the specimen retrieval pouch depicted in FIG. 1A with tissue partially contained within the specimen retrieval pouch;

FIG. 4 is a perspective view of the specimen retrieval pouch depicted in FIG. 1A with tissue fully contained within the specimen retrieval pouch; and FIG. 5 is a perspective view of a specimen retrieval device in accordance with another embodiment of the present disclosure.

DETAILED DESCRIPTION OF THE EMBODIMENTS

Figure 1A:
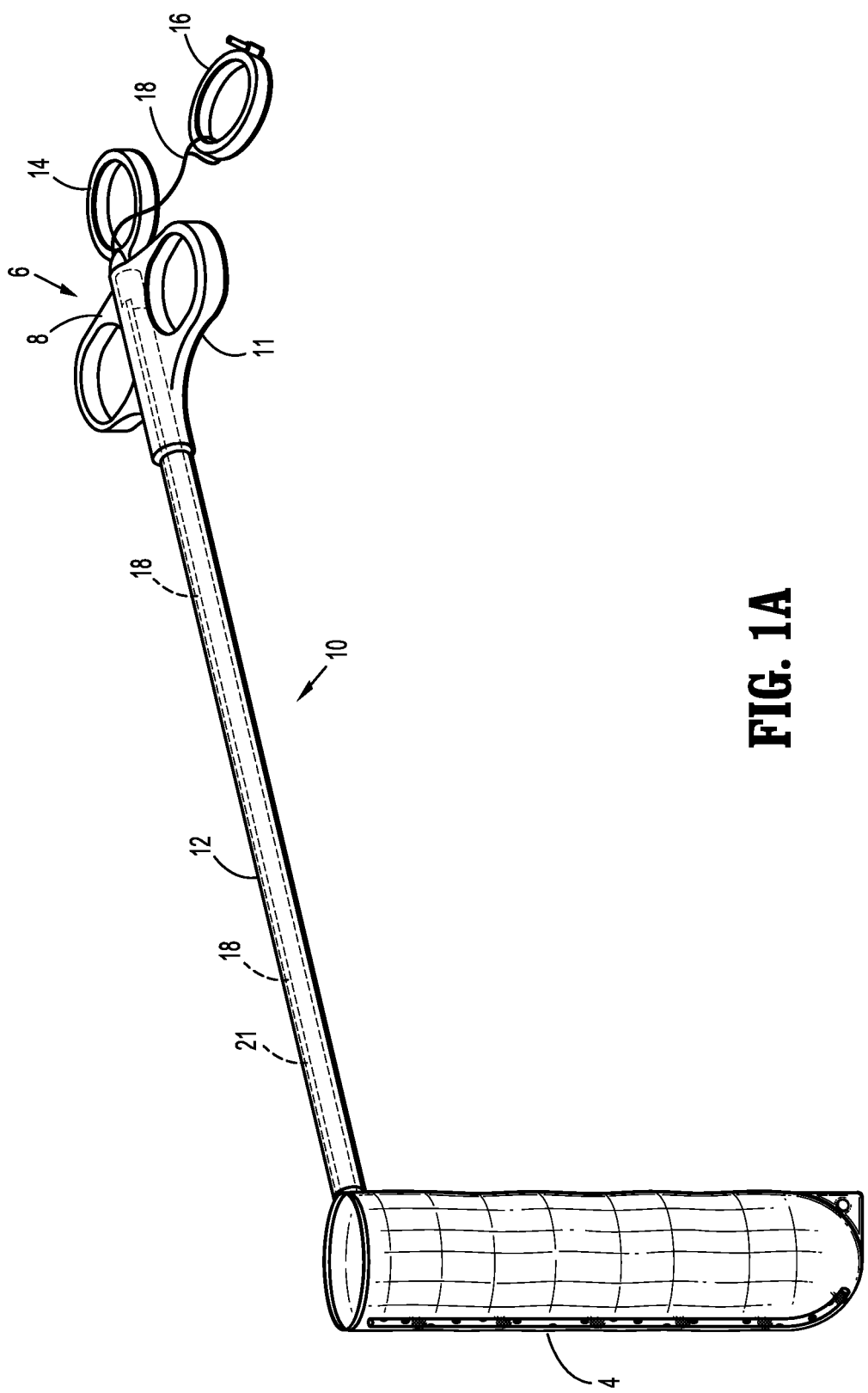
FIG. 1A is a perspective view of a specimen retrieval device and a specimen retrieval pouch in accordance with an embodiment of the present disclosure.

Embodiments of the present disclosure will now be described in detail with reference to the drawings, in which like reference numerals designate identical or corresponding elements in each of the several views. As used herein, the term distal refers to the portion of the instrument which is farthest from the user, while the term proximal refers to that portion of the instrument which is closest to the user. In the following description, well-known functions or constructions are not described in detail to avoid obscuring the present disclosure in unnecessary detail.

As used herein with reference to the present disclosure, the terms laparoscopic and endoscopic are interchangeable and refer to instruments having a relatively narrow operating portion for insertion into a cannula or a small incision in the skin. They also refer to minimally invasive surgical procedures. It is believed that the present disclosure may find use in any procedure where access to the interior of the body is limited to a relatively small incision, with or without the use of a cannula as in minimally invasive procedures.

With reference to FIGS. 1A-1B, a specimen retrieval device or applicator 10 including a specimen retrieval pouch assembly 4 (pouch 4) according to an embodiment of the present disclosure is illustrated. For illustrative purposes, pouch 4 is described herein as being deployable from the specimen retrieval device 10, although pouch 4 may be inserted through and, subsequently, removed from an opening in a patient without the use of the specimen retrieval device 10.

Briefly, specimen retrieval device 10 includes a handle assembly 6 that includes handle portions 8 and 11 (FIG. 1A) that are fixedly joined together. An elongated tube or shaft 12 extends from the handle assembly 6 and is dimensioned for insertion through a trocar cannula for endoscopic or laparoscopic procedures (FIG. 1A). In certain embodiments, the shaft 12 may be configured to articulate. A drive rod 21 extends within the shaft 12 and along a length thereof and operably couples to an actuator that is in the form of a finger loop 14 (FIG. 1A). A distal end of the drive rod 21 operably couples to the pouch 4 by suitable methods consistent for deploying the pouch 4 from the specimen retrieval device 10. Finger loop 14 is configured for engagement by a user's fingers and is configured to axially translate or move the drive rod 21 within the shaft 12. A pull ring 16 is operably coupled to a proximal end of a suture 18 by any suitable coupling method, e.g., tied, adhesive, etc., and is configured to facilitate pulling the suture 18 (FIG. 1A). In the illustrated embodiment, pull ring 16 releasably couples, via one or more suitable coupling methods, e.g., a press or friction fit, to the finger loop 14, see FIG. 1A in combination with FIG. 1B, for example.

With reference now to FIGS. 2-4, pouch 4 is shown. Pouch 4 may be made from any suitable biocompatible materials capable of forming a flexible membrane. More particularly, pouch 4 is constructed from one or more sheets of flexible film or sheet formed from a substantially transparent polymeric material. In the illustrated embodiment, pouch 4 is constructed from two sheets of plastic material that are joined together via one or more suitable joining methods, e.g., adhesives, welding, etc. In the illustrated embodiment, the two sheets of plastic material are welded together forming interior and exterior walls 30 and 32, respectively, (FIGS. 2-4). In the illustrated embodiment, interior wall 30 is textured to form a plurality of channels 36 (FIGS. 2 and 3) that are configured to allow air flow around tissue "T" positioned in the pouch 4 to prevent large areas of air entrapment from developing in the pouch 4 and adjacent to tissue "T." Pouch 4 is substantially impervious to penetration by cancer cells. Pouch 4 is proportioned for the purpose of organ entrapment or removal. In certain instances, the pouch 4 may be dimensioned and fabricated of a suitable material to allow treatment, e.g. morcellation or division, of the organ tissue, for example to reduce its bulk to facilitate withdrawal from the body cavity.

Pouch 4 includes a generally tubular or elongated configuration that is defined by a widened, opened upper portion or mouth 26 and a tapered, closed lower portion 28 (FIGS. 2-4). In certain embodiments, the mouth 26 may be openable and closable. That is, a drawstring or other suitable device may be operably coupled to the mouth 26 and configured to close the mouth upon actuation thereof, i.e., when the drawstring is pulled; this embodiment is particularly useful when the tissue "T" that is to be removed is diseased.

Continuing with reference to FIGS. 2-4, an elongated tube 34 includes open proximal and distal ends 35 and 37, respectively. The open proximal and distal ends 35 and 37 are configured to allow unrestricted movement of a suture 40 within the elongated tube 34. Additionally, distal end 37 is dimensioned to prevent a distal end 44 of the suture 40 from being pulled completely through the open distal end 37 and into the elongated tube 34.

Elongated tube 34 extends along a length of the pouch 4 (FIGS. 2-4). Elongated tube 34 is operably coupled to the interior wall 30 by one or more suitable coupling methods, e.g., welding, adhesives, overmolding etc. In the illustrated embodiment, elongated tube 34 is welded (illustrated by hatching "w" in FIGS. 2-4) at intermittent locations along the interior wall 30. Welding the elongated tube 34 in this manner along the interior wall 30 of the pouch 4 facilitates evacuating air from the pouch 4 and provides structural support to pouch 4 while tissue "T" is being drawn into the pouch 4.

Elongated tube 34 may be made from any suitable biocompatible material including, but not limited to plastic, metal, metal alloy. In the illustrated embodiment, elongated tube 34 is made from plastic. In the illustrated embodiment, the elongated tube 34 is made from a plastic that allows the pouch 4 to be inserted into and, subsequently, deployed from the surgical retrieval apparatus 10. For example, and in one particular embodiment, the plastic that the elongated tube 34 is made from allows the pouch 4 to be rolled (or folded) and loaded or placed within the elongated shaft 12 of the specimen retrieval device 10. Upon deployment of the pouch 4, the plastic that the elongated tube 34 is made from allows the pouch 4 including the elongated tube 34 to be unrolled (or unfolded).

A plurality of openings 38 (FIGS. 2-4) of suitable configuration are positioned along a length of the elongated tube 34. Openings 38 are configured to permit air therethrough when tissue "T" is being drawn into the pouch 4 to facilitate positioning the tissue "T" within the pouch 4. To this end, the openings 38 may be positioned radially along a length of the elongated tube 34 forming a generally spiral configuration (FIGS. 2-4) or other configurations. As tissue "T" enters the pouch 4, air is expelled through the openings 38 and communicated toward a proximal end of the pouch 4, thus, allowing the tissue "T" to fully enter the pouch 4 without the hindrance of air pockets forming in the pouch 4 and around tissue "T."

With reference again to FIGS. 2-4, suture 40 (or other suitable device) is operably coupled to the pouch 4 via the elongated tube 34. In particular, suture 40 is movable within the elongated tube 34 and with respect to the pouch 4 from a first position for attaching to tissue "T" (FIG. 2) to a subsequent position for drawing the tissue "T" into the pouch 4 (see FIGS. 3 and 4 for example) when the pull ring 16 is pulled.

Suture 40 is configured to secure to tissue "T" via one or more suitable securement methods to draw or pull the tissue "T" into the pouch 4. In one particular embodiment, such as the one illustrated in FIGS. 2-4, a needle 42 (or other suitable device, such as, for example, alligator clips, clamps, hooks, and the like) is operably coupled (via one or more suitable methods) to a distal end 44 of the suture 40. Alternatively, the distal end 44 may include a loop "L" of suitable configuration, see FIG. 5 for example. In this instance, the loop "L" is operable to attach to tissue "T." This embodiment is particularly useful when the tissue "T" that needs to be removed is diseased (e.g., cancerous tissue) in which case the tissue "T" cannot be punctured, i.e., to reduce the likelihood of infecting healthy tissue.

One or more reinforced tabs 46 (one reinforced tab 46 is shown in FIGS. 2-4) are operably disposed on the pouch 4 and are provided to counter a force being applied to the suture 40 as the suture 40 is being pulled through the elongated tube 34. In particular, the reinforced tab 46 is configured to be grasped by a user to provide a counter pull force as the suture 40 is being pulled through the elongated tube 34. For example, a grasper (or the like) may be utilized by a user to grasp the reinforced tab 46 while the suture 40 is pulled through the elongated tube 34. In the embodiment illustrated in FIGS. 2-4, the reinforced tab includes an aperture 48 that is provided to facilitate grasping, i.e., hooking, the reinforced tab 46. Reinforced tab 46 is operably disposed on the exterior wall 32 of the pouch 4 adjacent the closed bottom portion 28.

Reinforced tab 46 may be made from any suitable biocompatible material including, but not limited to, plastic, metal, metal alloy, etc. In the illustrated embodiment, the reinforced tab 46 is made from a plastic that is allows the pouch 4 to be inserted into and, subsequently, deployed from the surgical retrieval apparatus 10. For example, and in one particular embodiment, the plastic that the reinforced tab 46 is made from allows the pouch 4 to be rolled (or folded) and loaded or placed within the elongated shaft 12 of the specimen retrieval device 10. Upon deployment of the pouch 4, the plastic that the reinforced tab 46 is made from allows the pouch 4 including the reinforced tab 46 to be unrolled (or unfolded).

In one particular embodiment, such as the one illustrated in FIG. 5, the reinforced tab 46 may be replaced by two reinforced wings or segments 46a and 46b. Reinforced segments 46a and 46b function similar to reinforced tab 46. In addition, reinforced segments 46a and 46b provide additional support to the pouch 4 while tissue "T" is being drawn into the pouch 4. Moreover, the reinforced segments 46a and 46b are flexible and capable of sitting flush against the exterior wall 32 of the pouch 4. As can be appreciated, this may prove useful when the pouch 4 is positioned through an access opening without the use of the specimen retrieval device 10. In the embodiment illustrated in FIG. 5, each reinforced segment 46a and 46b defines respective rows of apertures 48a and 48b. Apertures 48a and 48b are operable to perform the same function as aperture 48.

In use, specimen retrieval device 10 is utilized to enter an access opening in a patient to position the pouch 4 within a body cavity of a patient. Subsequently, pouch 4 is deployed from the specimen retrieval device 10 and unrolled (FIG. 2). In one particular surgical scenario, a grasper may be utilized to help unroll the pouch 4. Once in the unrolled configuration, the grasper may be utilized to attach the distal end 44, either by needle 46 or loop "L," to a tissue specimen "T", e.g., tissue from the intestinal region. Thereafter, suture 40 is pulled through the elongated tube 34 via pull ring 16 to draw the tissue "T" into the pouch 4 (FIGS. 2-4). As tissue "T" is being drawn into the pouch 4, air is evacuated through the apertures 38 and/or the channels 36. In particular, air trapped in the pouch 4 is directed to the apertures 38 via the channels 36 and communicated toward the proximal end of the pouch 4. A user may grasp the reinforced tab 46 (or in some instances, one or both of the reinforced segments 46a and 46b) to facilitate pulling the tissue "T" into the pouch 4.

When tissue "T" is positioned adjacent the closed lower portion 28, a user may release the reinforced tab 46 (or reinforced tabs 46a and 46b) and pull the suture 40 to remove the pouch 4 including the tissue "T" contained therein. Open distal end 37 maintains distal end 44 of the suture 40 including tissue "T" attached thereto within the pouch 4 as the suture 40 is pulled. That is, the open distal end 37 is configured to prevent passage of the distal end 44 (with either the needle 42 or loop "L" coupled thereto) of the suture 40 therethrough and into the elongated tube 34.

When the pouch 4 is adjacent the access opening, a user may grasp the reinforced tab 46 (or tabs 46a and 46b) to pull out the pouch 4 through access opening. Alternatively, a user can simply use the suture 40 to pull out the pouch 4 through access opening.

The unique configuration of the elongated tube 34 with the suture 40 positioned therein overcomes the aforementioned drawbacks that are typically associated with conventional specimen retrieval pouches. That is, elongated tube 34 with the suture 40 positioned therein allows a user to pull the tissue "T" into the pouch 4 from the lower closed portion 28 and, thus, reduces, if not eliminates, the likelihood of the tissue "T" gathering or bulging within the pouch 4. Moreover, the apertures 38 and/or channels 36 reduce, if not eliminate, air entrapment within the pouch 4. Further, the reinforced tab 46 (or tabs 46a and 46b) provides an additional and/or an alternative method for removing the pouch 4 from the access opening; this may prove advantageous when large tissue segments or organs are contained in the pouch 4. That is, removing the pouch 4 with large tissue "T" contained therein by way of pulling the pouch 4 by the reinforced tab 46 (or tabs 46a and 46b) and not by pulling the suture 40 reduces the likelihood of the pouch 4 tearing or ripping along the elongated tube 34 as the pouch 4 is pulled through the access opening.

From the foregoing and with reference to the various figure drawings, those skilled in the art will appreciate that certain modifications can also be made to the present disclosure without departing from the scope of the same. For example, and as noted above, it may prove advantageous to provide the pouch 4 with a closable and openable top portion 26. In this instance, the specimen retrieval device 10 may be equipped with a drawstring (not shown) that is configured to operably couple to the pouch 4. Specimen retrieval devices that include drawstrings are well known in the art. One such specimen retrieval device that may be utilized with the pouch 4 is disclosed in commonly-owned U.S. Pat. No. 5,647,372 to Tovey et al., filed on Sep. 16, 1994, the entirety of which being incorporated herein by reference. In this instance, and as can be appreciated, certain modifications to pouch 4 may need to be made in order for the pouch 4 to function in a manner as described herein. For example, the open top portion 26 of the pouch 4 may need to be perforated or scored.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A specimen retrieval pouch, comprising:
    a wall including:
        a closed bottom portion; and
        an open upper portion;
    an elongated tube intermittently connected to the wall and extending along a length thereof, the elongate tube having a distal portion connected to the closed bottom portion of the wall;
    a suture positioned within the elongated tube, the suture being movable within the elongated tube relative to the wall; and
    a securement device secured to one end of the suture, the securement device being configured to be secured to tissue to draw tissue into the specimen retrieval pouch when the suture is pulled through the elongated tube.

2. The specimen retrieval pouch according to claim 1, wherein the elongated tube includes a plurality of openings positioned along a length thereof.

3. The specimen retrieval pouch according to claim 1, wherein the securement device extends distally beyond the distal portion of the elongated tube.

4. The specimen retrieval pouch according to claim 1, wherein the wall includes an interior wall and a plurality of channels defined by and in the wall, the channels being configured to allow air flow therethrough.

5. The specimen retrieval pouch according to claim 1, further comprising:
    at least one reinforced tab configured to be grasped by a user to provide a counter pull force as the suture is being pulled through the elongated tube, wherein the wall includes:
        an exterior wall, the at least one reinforced tab being operably disposed on the exterior wall.

6. The specimen retrieval pouch according to claim 1, wherein the wall has a width that tapers from the open upper portion toward the closed bottom portion.

7. The specimen retrieval pouch according to claim 1, wherein the elongated tube has an open proximal portion disposed within the open upper portion of the wall.

8. A specimen retrieval device, comprising
    a specimen retrieval pouch including:
        an interior wall having:
            a closed bottom portion; and
            an open upper portion; and
        an elongated tube connected to the interior wall and extending along a length thereof, the elongated tube including:
            a proximal portion disposed adjacent the open upper portion of the wall;
            a distal portion connected to the closed bottom portion of the wall; and
            a plurality of openings positioned along a length of the elongated tube; and
        a suture positioned within the elongated tube and configured for drawing tissue into the specimen retrieval pouch when the suture is pulled through the elongated tube.

9. The specimen retrieval device according to claim 8, wherein the suture includes a securement device secured to a distal portion of the suture and extends distally beyond the distal portion of the elongated tube.

10. The specimen retrieval device according to claim 8, further comprising:
    at least one reinforced tab configured to be grasped by a user to provide a counter pull force as the suture is being pulled through the elongated tube, wherein the specimen retrieval pouch further includes:
        an exterior wall in abutment with the interior wall, the at least one reinforced tab being operably disposed on the exterior wall.

11. The specimen retrieval device according to claim 8, wherein the wall includes a plurality of channels defined by and in the wall, the channels being configured to allow air flow therethrough.

12. The specimen retrieval device according to claim 8, wherein the specimen retrieval pouch is wider at the open upper portion and tapers toward the closed bottom portion.

13. The specimen retrieval device according to claim 8, wherein the elongated tube is intermittently connected to the interior wall.

14. A specimen retrieval device, comprising
    an applicator;
    a specimen retrieval pouch operably disposed within the applicator and deployable therefrom, the specimen retrieval pouch including:
        a wall having:
            a closed bottom portion;
            an open upper portion; and
            a plurality of channels defined by and in an inner surface of the wall, the channels being configured to allow air flow therethrough; and
        an elongated tube connected to the wall and extending along a length thereof, the elongated tube having a distal portion connected to the closed bottom portion of the wall;
    and
    a suture positioned within the elongated tube, the suture being movable within the elongated tube relative to the specimen retrieval pouch for drawing tissue into the specimen retrieval pouch via the open upper portion when the suture is pulled.

15. The specimen retrieval device according to claim 14, wherein the elongated tube is intermittently connected to the wall.

16. The specimen retrieval device according to claim 14, wherein the elongated tube has a plurality of openings positioned along a length thereof.

* * * * *